(12) United States Patent
Southard et al.

(10) Patent No.: US 9,446,077 B2
(45) Date of Patent: Sep. 20, 2016

(54) FASCIA FIBROUS COMPOSITIONS AND METHODS FOR THEIR USE AND MANUFACTURE

(71) Applicant: AlloSource, Centennial, CO (US)

(72) Inventors: Matthew Southard, Denver, CO (US); Adrian C. Samaniego, Parker, CO (US); Peter J. Stevens, N. Richland Hills, TX (US)

(73) Assignee: AlloSource, Centennial, CO (US)

( * ) Notice: Subject to any disclaimer, the term of this patent is extended or adjusted under 35 U.S.C. 154(b) by 0 days.

(21) Appl. No.: 14/204,346

(22) Filed: Mar. 11, 2014

(65) Prior Publication Data

US 2014/0271790 A1    Sep. 18, 2014

Related U.S. Application Data

(60) Provisional application No. 61/779,269, filed on Mar. 13, 2013.

(51) Int. Cl.
*A61K 35/35* (2015.01)
*D01C 3/00* (2006.01)

(52) U.S. Cl.
CPC .............. *A61K 35/35* (2013.01); *D01C 3/00* (2013.01)

(58) Field of Classification Search
None
See application file for complete search history.

(56) References Cited

U.S. PATENT DOCUMENTS

| | | |
|---|---|---|
| 4,361,552 A | 11/1982 | Baur |
| 5,336,616 A | 8/1994 | Livesey et al. |
| 5,556,379 A | 9/1996 | Wolfinbarger |
| 5,723,010 A | 3/1998 | Yui et al. |
| 5,797,871 A | 8/1998 | Wolfinbarger |
| 5,820,581 A | 10/1998 | Wolfinbarger |
| 5,837,278 A | 11/1998 | Geistlich et al. |
| 5,876,451 A | 3/1999 | Yui et al. |
| 5,976,104 A | 11/1999 | Wolfinbarger |
| 5,977,034 A | 11/1999 | Wolfinbarger |
| 5,977,432 A | 11/1999 | Wolfinbarger |
| 5,989,498 A | 11/1999 | Odland |
| 6,024,735 A | 2/2000 | Wolfinbarger |
| 6,152,142 A | 11/2000 | Tseng |
| 6,189,537 B1 | 2/2001 | Wolfinbarger |
| 6,305,379 B1 | 10/2001 | Wolfinbarger |

(Continued)

FOREIGN PATENT DOCUMENTS

| | | |
|---|---|---|
| WO | 2011/072393 A1 | 6/2011 |
| WO | 2012083021 A1 | 6/2012 |

(Continued)

OTHER PUBLICATIONS

International Search Report and Written Opinion for PCT/US2014/023737, mailed on Jul. 14, 2014, 12 pages.

*Primary Examiner* — Sue Liu
*Assistant Examiner* — Thor Nielsen
(74) *Attorney, Agent, or Firm* — Kilpatrick Townsend & Stockton LLP

(57) ABSTRACT

Embodiments of the present invention encompass fascia, fat, and dermis fibrous compositions, and methods for their manufacture and use. In a first aspect, embodiments of the present invention encompass methods for obtaining a fascia fiber for use in producing a biotextile. Exemplary methods may include treating a cadaveric fascia tissue with acetone, and obtaining the fascia fibers from the treated fascia tissue. In some cases, methods may include processing the fascia fibers to produce the fibrous fascia biotextile.

35 Claims, 18 Drawing Sheets

(56) References Cited

U.S. PATENT DOCUMENTS

| | | |
|---|---|---|
| 6,326,019 B1 | 12/2001 | Tseng |
| 6,432,710 B1 | 8/2002 | Boss |
| 6,752,834 B2 | 6/2004 | Geistlich et al. |
| 6,837,907 B2 | 1/2005 | Wolfinbarger |
| 7,153,518 B2 | 12/2006 | Wironen et al. |
| 7,347,876 B2 | 3/2008 | Tsai |
| 7,393,437 B2 | 7/2008 | Chan |
| 7,494,802 B2 | 2/2009 | Tseng |
| 7,723,108 B2 | 5/2010 | Truncale et al. |
| 7,727,550 B2 | 6/2010 | Siegal et al. |
| 7,824,671 B2 | 11/2010 | Binder |
| 7,902,145 B2 | 3/2011 | Chu |
| 7,981,022 B2 | 7/2011 | Gellman et al. |
| 8,021,692 B2 | 9/2011 | Hiles |
| 8,058,066 B2 | 11/2011 | Marshall |
| 8,071,135 B2 | 12/2011 | Liu et al. |
| 8,105,634 B2 | 1/2012 | Liu et al. |
| 8,153,162 B2 | 4/2012 | Tseng |
| 8,158,141 B2 | 4/2012 | Chen |
| 8,158,379 B2 | 4/2012 | Ronholdt |
| 8,168,215 B2 | 5/2012 | Dufrane et al. |
| 8,182,840 B2 | 5/2012 | Tseng |
| 8,182,841 B2 | 5/2012 | Tseng |
| 8,187,639 B2 | 5/2012 | Tseng |
| 8,198,245 B2 | 6/2012 | Niklason |
| 8,231,908 B2 | 7/2012 | Kinoshita |
| 8,309,106 B2 | 11/2012 | Masinaei et al. |
| 8,323,701 B2 | 12/2012 | Daniel et al. |
| 8,357,402 B2 | 1/2013 | Ingram et al. |
| 8,357,403 B2 | 1/2013 | Daniel et al. |
| 8,372,437 B2 | 2/2013 | Daniel |
| 8,372,438 B2 | 2/2013 | Daniel et al. |
| 8,372,439 B2 | 2/2013 | Daniel et al. |
| 8,409,626 B2 | 4/2013 | Daniel |
| 8,420,126 B2 | 4/2013 | Tseng |
| 8,440,235 B2 | 5/2013 | Tseng |
| 8,455,009 B2 | 6/2013 | Tseng et al. |
| 8,460,714 B2 | 6/2013 | Tseng et al. |
| 8,642,092 B2 | 2/2014 | Daniel et al. |
| 8,703,206 B2 | 4/2014 | Daniel et al. |
| 8,703,207 B2 | 4/2014 | Daniel et al. |
| 8,709,493 B2 | 4/2014 | Daniel et al. |
| 8,709,494 B2 | 4/2014 | Daniel |
| 8,822,415 B2 | 9/2014 | Trumpower et al. |
| 8,834,928 B1 | 9/2014 | Truncale et al. |
| 8,883,210 B1 | 11/2014 | Truncale et al. |
| 9,265,800 B2 | 2/2016 | Daniel |
| 9,265,801 B2 | 2/2016 | Daniel |
| 9,272,003 B2 | 3/2016 | Daniel et al. |
| 9,272,005 B2 | 3/2016 | Daniel |
| 2004/0048796 A1 | 3/2004 | Hariri |
| 2005/0019865 A1 | 1/2005 | Kihm |
| 2005/0058631 A1 | 3/2005 | Kihm |
| 2006/0234376 A1 | 10/2006 | Mistry |
| 2007/0160588 A1 | 7/2007 | Kihm |
| 2008/0046095 A1 | 2/2008 | Daniel |
| 2009/0258082 A1 | 10/2009 | Nikaido et al. |
| 2010/0112543 A1 | 5/2010 | Ngo |
| 2010/0124776 A1 | 5/2010 | Shi |
| 2010/0196478 A1 | 8/2010 | Masters |
| 2010/0304487 A1 | 12/2010 | Truncale |
| 2011/0091434 A1 | 4/2011 | Miller |
| 2011/0104100 A1 | 5/2011 | Riordan |
| 2011/0160857 A1 | 6/2011 | Bracone |
| 2011/0206776 A1 | 8/2011 | Tom et al. |
| 2011/0211523 A1 | 9/2011 | Seo et al. |
| 2011/0256202 A1 | 10/2011 | Tom et al. |
| 2011/0262393 A1 | 10/2011 | Yang |
| 2012/0009644 A1 | 1/2012 | Hanby et al. |
| 2012/0009679 A1 | 1/2012 | Hanby et al. |
| 2012/0010725 A1 | 1/2012 | Hamby et al. |
| 2012/0063997 A1 | 3/2012 | Hunter |
| 2012/0078378 A1 | 3/2012 | Daniel et al. |
| 2012/0083900 A1 | 4/2012 | Samaniego et al. |
| 2012/0141595 A1 | 6/2012 | Tseng et al. |
| 2012/0142102 A1 | 6/2012 | Chen |
| 2012/0164114 A1 | 6/2012 | Abbot |
| 2012/0189583 A1 | 7/2012 | Liu et al. |
| 2012/0189586 A1 | 7/2012 | Harrell |
| 2012/0191184 A1 | 7/2012 | Chen |
| 2012/0201787 A1 | 8/2012 | Abbot |
| 2012/0225484 A1 | 9/2012 | Bhatia et al. |
| 2012/0269774 A1 | 10/2012 | Ichim |
| 2012/0276080 A1 | 11/2012 | Kinoshita et al. |
| 2012/0276150 A1 | 11/2012 | Lauritzen et al. |
| 2012/0294810 A1 | 11/2012 | Daniel |
| 2012/0294811 A1 | 11/2012 | Daniel |
| 2012/0294908 A1 | 11/2012 | Daniel et al. |
| 2012/0294910 A1 | 11/2012 | Daniel et al. |
| 2012/0310367 A1 | 12/2012 | Connor |
| 2012/0328690 A1 | 12/2012 | Tseng et al. |
| 2013/0004465 A1 | 1/2013 | Aberman |
| 2013/0006385 A1 | 1/2013 | Daniel |
| 2013/0052169 A1 | 2/2013 | Marom |
| 2013/0202676 A1 | 8/2013 | Koob et al. |
| 2013/0218274 A1 | 8/2013 | Spencer et al. |
| 2013/0230561 A1 | 9/2013 | Daniel et al. |
| 2013/0344162 A1 | 12/2013 | Morse et al. |
| 2014/0017280 A1 | 1/2014 | Daniel et al. |
| 2014/0050788 A1 | 2/2014 | Daniel et al. |
| 2014/0052247 A1 | 2/2014 | Daniel et al. |
| 2014/0052274 A1 | 2/2014 | Koob et al. |
| 2014/0106447 A1 | 4/2014 | Brown et al. |
| 2014/0140964 A1 | 5/2014 | Brown et al. |
| 2014/0205646 A1 | 7/2014 | Morse et al. |
| 2014/0214176 A1 | 7/2014 | Daniel et al. |
| 2014/0234387 A1 | 8/2014 | Daniel et al. |
| 2014/0255496 A1 | 9/2014 | Daniel et al. |
| 2014/0255508 A1 | 9/2014 | Morse et al. |
| 2015/0140114 A1 | 5/2015 | Sasko |

FOREIGN PATENT DOCUMENTS

| | | |
|---|---|---|
| WO | 2012083023 A1 | 6/2012 |
| WO | 2012088396 A2 | 6/2012 |
| WO | 2012112410 | 8/2012 |
| WO | 2012112417 | 8/2012 |
| WO | 2012112441 | 8/2012 |
| WO | 2012116372 A1 | 8/2012 |
| WO | 2012136701 A1 | 10/2012 |
| WO | 2012170905 A1 | 12/2012 |
| WO | 2013032938 A1 | 3/2013 | ic # FASCIA FIBROUS COMPOSITIONS AND METHODS FOR THEIR USE AND MANUFACTURE

CROSS-REFERENCES TO RELATED APPLICATIONS

This application claims the benefit of U.S. Provisional Application No. 61/779,269 filed Mar. 13, 2013, the entire contents of which are incorporated herein by reference for all purposes.

BACKGROUND OF THE INVENTION

Embodiments of the present invention relate generally to the field of allogeneic transplants, and in particular to allograft compositions containing fascia, fat, or dermis tissue, and methods for their use and manufacture.

Human tissue compositions, which may be derived from cadaveric donors, have been used for many years in various surgical procedures. Allograft and autograft tissue are both derived from humans; the difference is that allograft is harvested from an individual (e.g. donor) other than the one (e.g. patient) receiving the graft. Allograft tissue is often taken from cadavers that have donated their bodies so their tissue can be used for living people who are in need of it, for example, patients who are undergoing surgery for various reasons. Such tissues represent a gift from the donor or the donor family to enhance the quality of life for other people Although human tissue compositions and methods are presently available and provide real benefits to patients in need thereof, many advances may still be made to provide improved graft compositions and methods for their use and manufacture. The fibrous fascia compositions and treatment and manufacture methods described herein provide further solutions and answers to at least some of these outstanding needs.

BRIEF SUMMARY OF THE INVENTION

Fascia tissue includes layers of fibrous material within the body that surround muscles and other anatomical features. For example, an abundance of fascia connective tissue can be found at the quadriceps and inner or frontal thigh areas. Typically, fascia is flexible and contains collagen fibers which have been formed by fibroblasts.

Embodiments of the present invention encompass techniques for developing fibers or filaments from fascia, processing the fibers or filaments into surgical products, and administering such products to recipient patients.

In a first aspect, embodiments of the present invention encompass methods for obtaining a fascia fiber for use in producing a biotextile. Exemplary methods may include treating a cadaveric fascia tissue with acetone, and obtaining the fascia fibers from the treated fascia tissue.

In another aspect, embodiments of the present invention encompass methods of producing a fibrous fascia biotextile composition. Exemplary methods include obtaining a cadaveric fascia tissue, treating the cadaveric fascia tissue with an organic solvent such as acetone, obtaining fascia fibers from the treated cadaveric fascia tissue, and processing the fascia fibers to produce the fibrous fascia biotextile.

In yet another aspect, embodiments of the present invention encompass fibrous fascia biotextile compositions that include a plurality of cadaveric fascia tissue fibers. Such fibers may be obtained from a cadaveric fascia tissue treated with acetone, or another organic solvent.

In a further aspect, embodiments of the present invention encompass methods for treating a patient with a fibrous fascia biotextile composition. Exemplary methods include obtaining a fibrous fascia biotextile composition, and applying or administering the composition to a treatment site of the patient. Biotextile compositions may include one or more fascia tissue fibers obtained from an acetone-treated or organic solvent-treated cadaveric fascia tissue.

In another aspect, embodiments of the present invention include a method of producing a fibrous biotextile composition. The method may include obtaining a cadaveric fat tissue. The method may include treating the cadaveric fat tissue with hexane. In these or other embodiments, the method may include obtaining fat fibers from the treated cadaveric fat tissue. In some cases, the method may include processing the fat fibers to produce the fibrous biotextile composition. In these or other embodiments, the method may include treating the cadaveric fat tissue with acetone before treating the cadaveric fat tissue with hexane.

In a further aspect, embodiments of the present invention may encompass a method of producing a fibrous biotextile composition. The method may include obtaining a cadaveric dermis tissue. In these or other embodiments, the method may include treating the cadaveric dermis tissue with acetone. In some cases, the method may involve obtaining fibers from the treated cadaveric dermis tissue. The method may include processing the fibers to produce the fibrous biotextile composition.

In another aspect, embodiments of the present invention may encompass a method of producing a fibrous biotextile composition. The method may include obtaining a cadaveric tissue. In these or other embodiments, the method may include treating the cadaveric tissue with a solvent. In some cases, the method may involve obtaining fibers from the treated cadaveric tissue. The method may include processing the fibers to produce the fibrous biotextile composition. In these or other embodiments, the cadaveric tissue may include fascia tissue or dermis tissue. In some embodiments, the solvent may include acetonitrile.

In yet another aspect, embodiments of the present invention may encompass a fibrous biotextile composition. The fibrous biotextile composition may include a plurality of cadaveric fat tissue fibers. In some cases, the fibrous biotextile composition may include fibers that are obtained from a cadaveric fat tissue treated with hexane. In some embodiments, the composition may be substantially free of adipose oil or other oils.

In another aspect, embodiments of the present invention may encompass a fibrous biotextile composition. The fibrous biotextile composition may include a plurality of cadaveric dermis tissue fibers. In some cases, the fibrous biotextile composition may include fibers that are obtained from a cadaveric dermis tissue treated with acetone. In these or other embodiments, the composition may be substantially free of adipose oil or other oils.

In a further aspect, embodiments of the present invention may encompass a method of treatment a patient with a fibrous biotextile composition. The method may include applying the fibrous biotextile composition to a treatment site of the patient. In some embodiments, the composition may include a plurality of fat tissue fibers obtained from a hexane-treated cadaveric fat tissue.

In another aspect, embodiments of the present invention may include a method of treating a patient with a fibrous biotextile composition. The method may include applying the fibrous biotextile composition to a treatment site of the patient. In some cases, the composition may include a plurality of dermis tissue fibers obtained from an acetone-treated cadaveric dermis tissue.

The above described and many other features and attendant advantages of embodiments of the present invention will become apparent and further understood by reference to the following detailed description when considered in conjunction with the accompanying drawings.

DETAILED DESCRIPTION OF THE INVENTION

The fascia may refer to a fibrous membrane which covers most major muscles, nerves, and organs. Embodiments of the present invention encompass cadaveric fascia graft compositions, and methods for their use and manufacture. For example, fascia tissue can provide a biologically derived fibrous source of collagen that can be further manufactured or processed into predetermined various configurations, such as fascia fiber, fascia collagen bundles, fascia wires, fascia sheets, fascia filaments, and the like.

Figure 1:
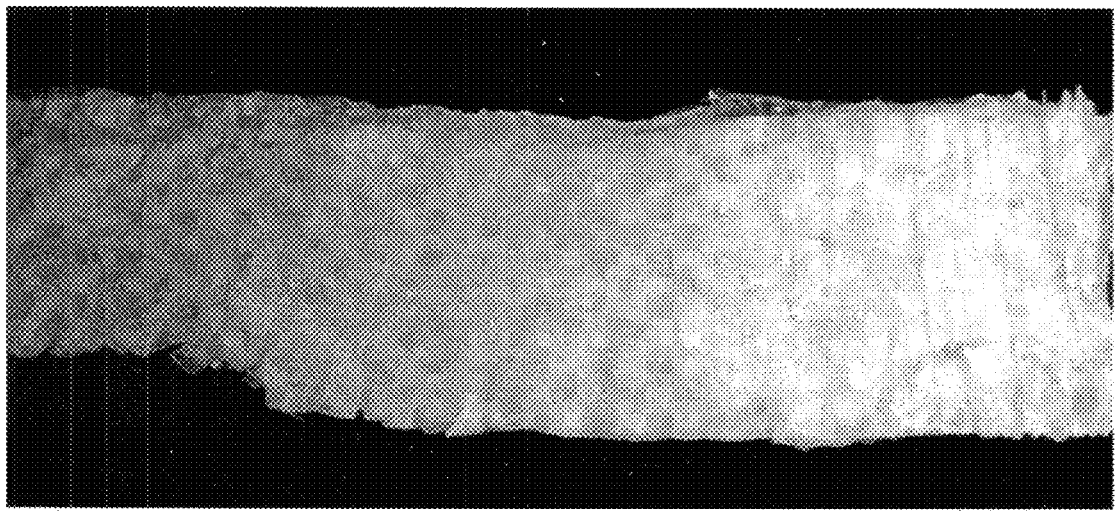
FIG. 1 shows the side of a piece of fascia that faces toward the muscle tissue when in a cadaveric donor individual.
Figure 2:
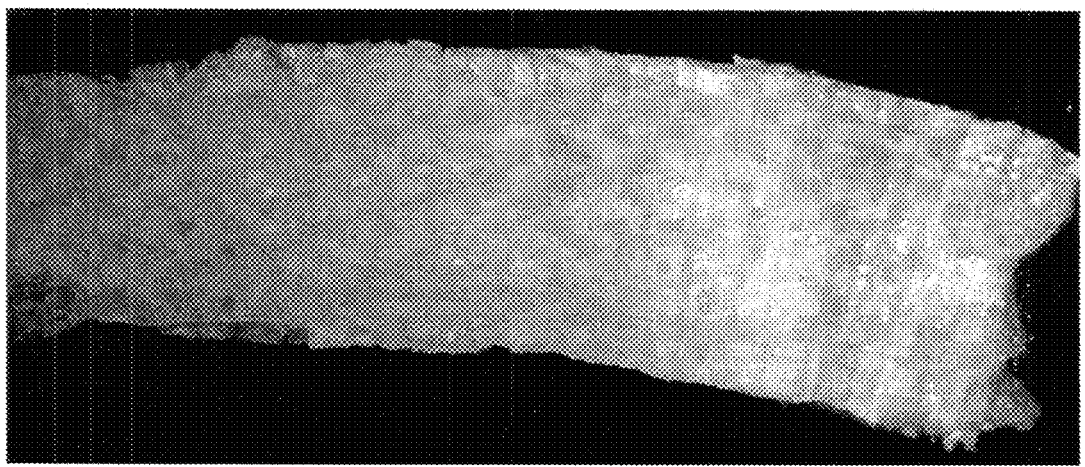
FIG. 2 shows the side of a piece of fascia that faces away from the muscle tissue when in a cadaveric donor individual.

Turning now to the drawings, FIGS. 1 and 2 depict a piece of fascia harvested from a cadaveric donor. The fascia piece has been substantially cleared of adipose and cleaned. As shown here, there is an orientation to the fascia tissue. FIG. 1 shows the side of the fascia that faces toward the muscle tissue when in the cadaveric donor individual. As depicted here, there are adipose lumps on the surface. FIG. 2 shows the opposing side of the fascia (facing away from the muscle). As depicted here, the surface has a shiny appearance. The dimension of the fascia piece is 1 cm×3 cm, and is shown at 0.5× magnification. The fascia is shown in a natural state.

Figure 3:
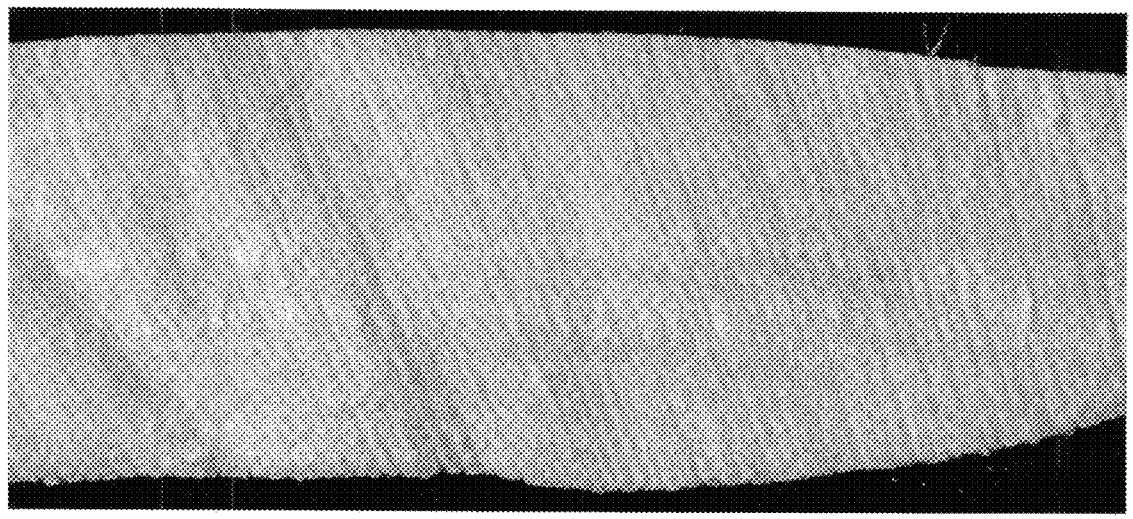
FIG. 3 shows a 1 cm×3 cm piece of fascia that has been submerged in acetone for 15 minutes and then air dried.
Figure 4:
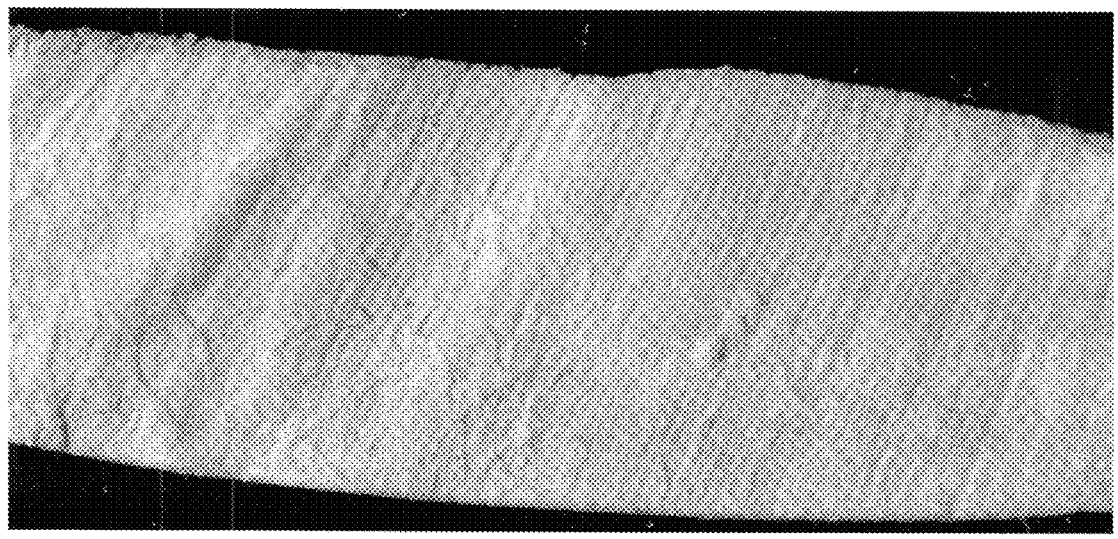
FIG. 4 shows a 1 cm×3 cm piece of fascia that has been submerged in acetone and then air dried.

As discussed elsewhere herein, fascia tissue can be processed to provide a fibrous material. For example, FIG. 3 shows a 1 cm×3 cm piece of fascia, which has been submerged in acetone for 15 minutes and then air dried. The side depicted here is that which faces away from the muscle (analogous to FIG. 2). The processed fascia includes larger primary fibers that are approximately 100 microns to 200 microns in diameter, which can be seen through a secondary layer of smaller fibers that coat the interior and exterior of the fascia and are mainly orientated at about 90 degrees to primary fibers. The inner and outer layer of smaller fibers average about 12 microns in diameter and are more randomly oriented than the larger primary fibers. The acetone treatment operates to dehydrate the fascia tissue, and also renders the fascia with a unique fibrous structure. FIG. 4 also shows a 1 cm×3 cm piece of fascia, which has been submerged in acetone and then air dried. The side depicted here is that which faces toward the muscle (analogous to FIG. 1). As depicted here, there are dehydrated areas of adipose matrix which are visible in the lower left region of the acetone dried graft (e.g. having the appearance of X's). Both FIGS. 3 and 4 are shown at a 0.5× magnification.

Subsequent to an acetone treatment, the fascia tissue can be pulled apart or otherwise processed to expose fibers ranging in diameter from 5 micron to 200 microns. The length of the fibers can correspond to a dimension of the fascia piece from which they are obtained (e.g. width, length, thickness). In addition to large fibers, there are spider web-like fibers which appear to help keep the fascia together. It has been found that the use of acetone is particularly effective in providing a processed fibrous fascia tissue wherein fibers of the processed fascia can be relatively easily harvested. Fascia can be recovered from any of a variety of sources from within the body, for example the inner or frontal thigh. In some cases, recovered tendon and/or ligament tissues can be processed according to techniques described herein to provide fibrous materials for use in biotextile manufacturing.

Figure 5:
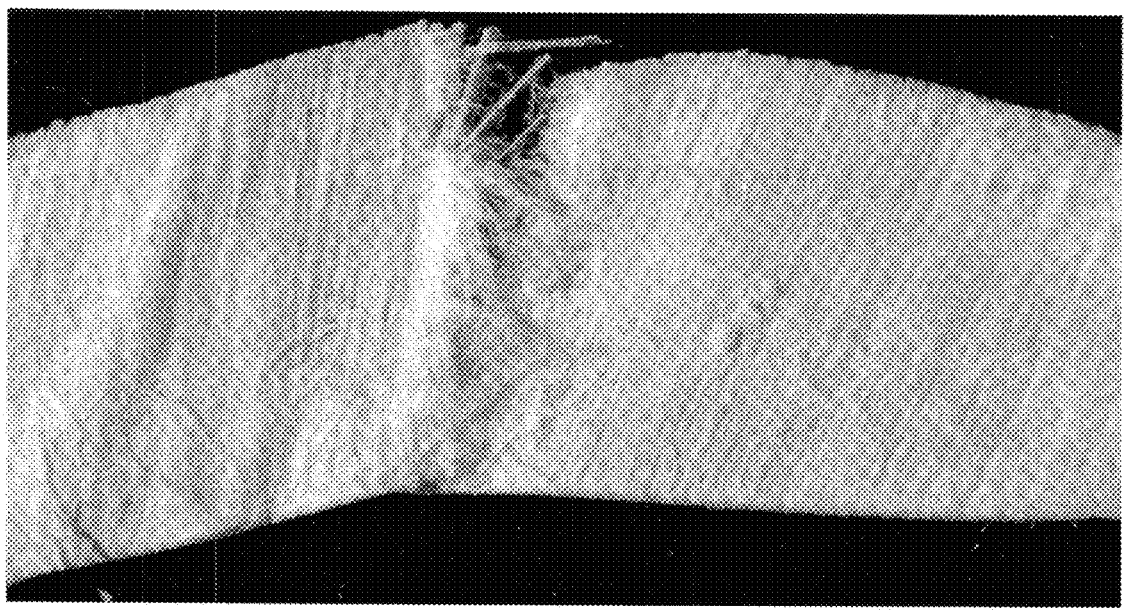
FIG. 5 depicts a strip of acetone-processed fascia that has been partially ripped apart.
Figure 6:
FIG. 6 shows a 10× magnification of the major fibers of a processed tissue.

FIG. 5 depicts a strip of acetone-processed fascia, which has been partially ripped apart, thus exposing a fibrous structure of the processed tissue. As illustrated here, the fibers are intact and easily separable from one another. FIG. 6 shows a 10× magnification of the major fibers, which are exposed in FIG. 5. Hence, as discussed elsewhere herein, tissue can be harvested from cadavers, and washed and cleaned of any biological fluids. The tissue can also be cleared of any cells and cell contents with a basic solution and subjected to an organic dehydrating solution which unravels the macrostructure of the fascia, leaving behind a fibrous matrix that can be processed by conventional textile fiber technology into a fiber that is ready to be weaved, bundled, spun, or otherwise further processed to provide any of a variety of biotextile configurations.

Figure 7:
FIG. 7 shows a 10× magnification of the major fibers of a piece of fascia that has been submerged in acetone and then air dried.
Figure 8:
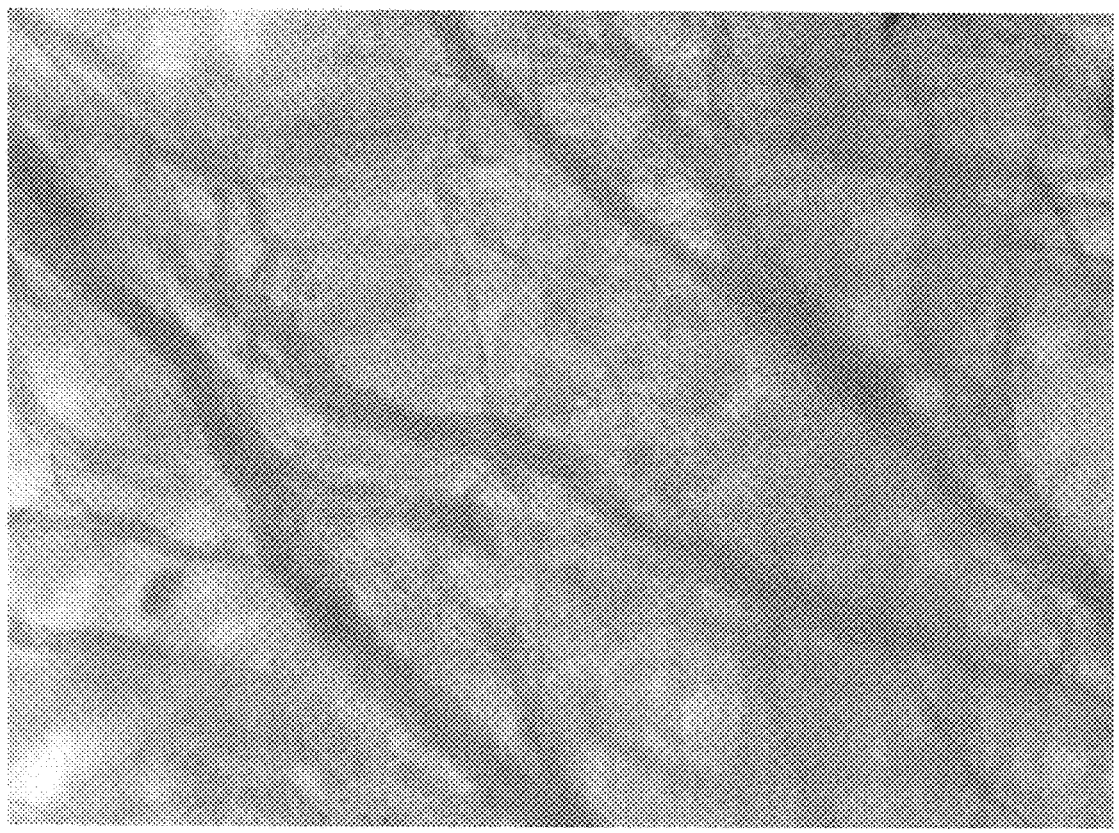
FIG. 8 shows a 10× magnification of the surface of tissue that has been submerged in acetone and then air dried.

FIG. 7 shows a 10× magnification of the major fibers depicted in FIGS. 3 and 4. As shown here, fibers may be present in a ribbed stalk form (e.g. center of FIG. 7). FIG. 8 shows a 10× magnification of the surface of the tissue depicted in FIGS. 3 and 4. As shown here, there are fibers having a spider web-like appearance.

Figure 9:
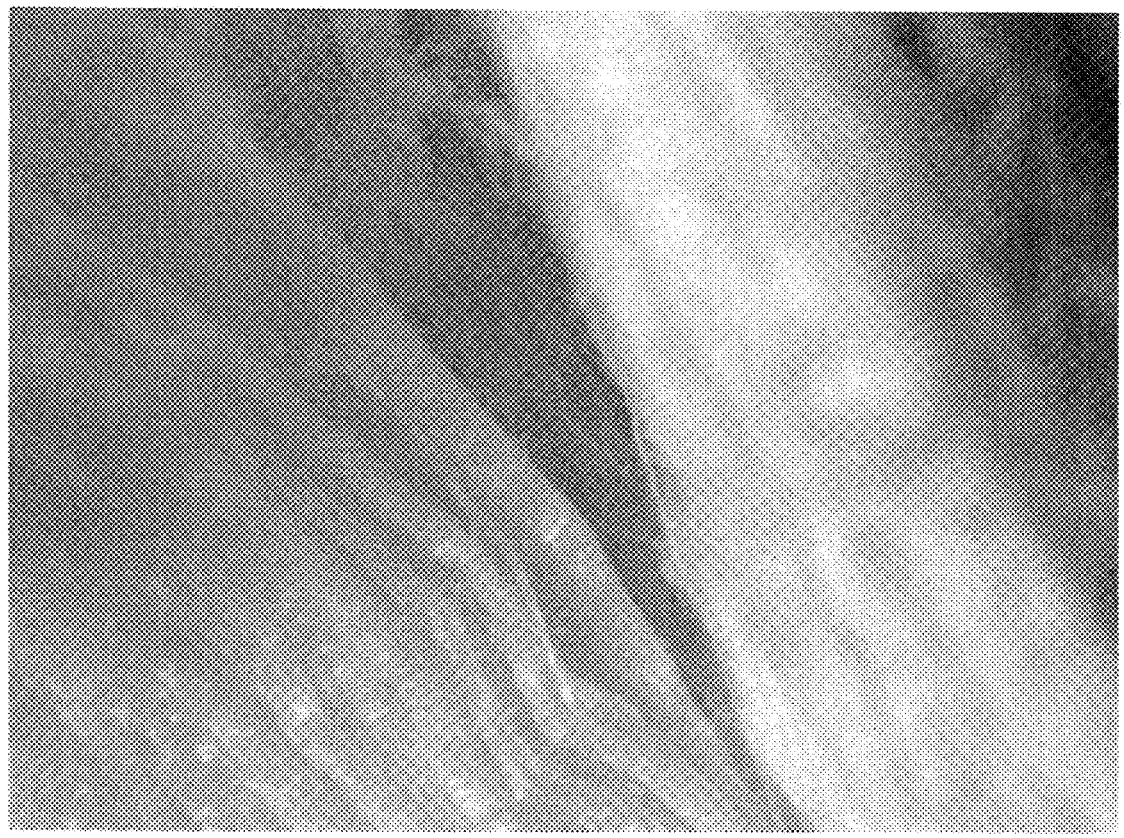
FIG. 9 shows a 0.5× intermediate stage view where the outer and inner layer of fibers separate.

FIG. 9 shows a 0.5× intermediate stage view where the outer and inner layer of fibers separate and there is a very distinct change in the structure of fascia fibers. The finer fibers can be characterized as spider web-like sheets or structures, and the larger fibers can be characterized as major or primary fibers.

Figure 10:
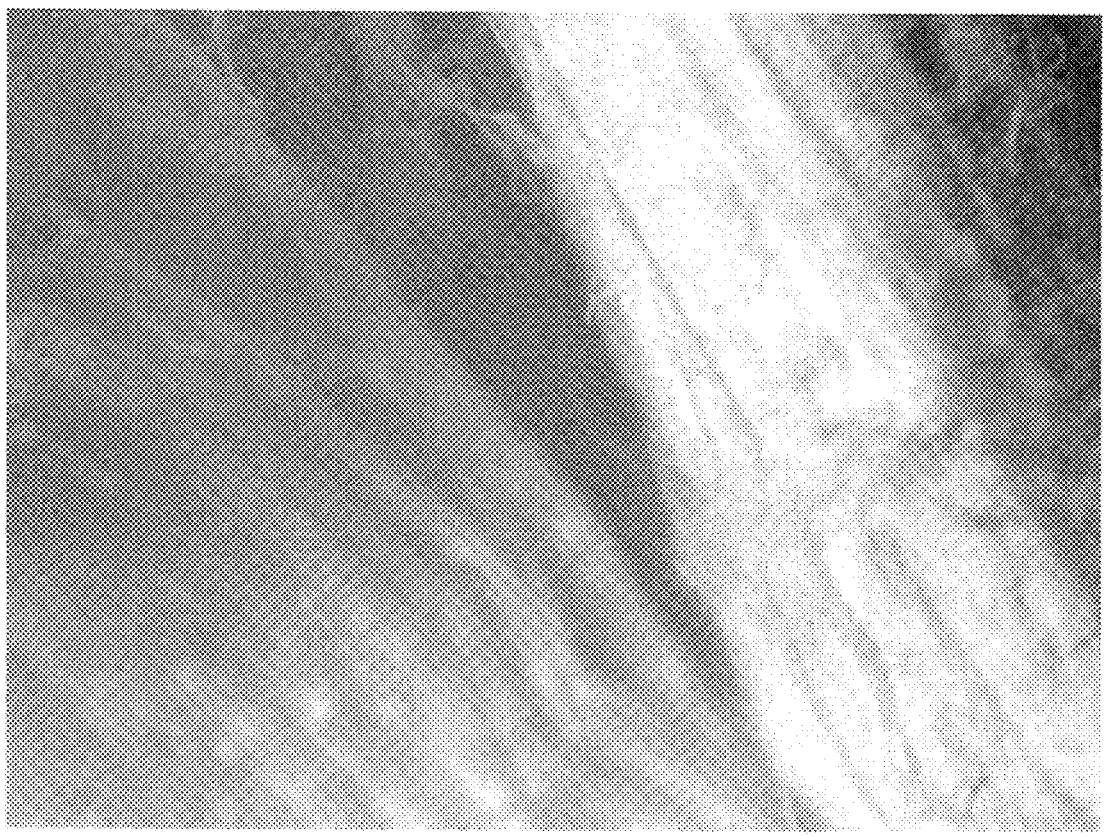
FIG. 10 shows a 0.5× intermediate stage view where the outer and inner layer of fibers separate.

FIG. 10 shows another 0.5× magnification view, detailing the smaller fibers on the spider web-like sheet covering the major fibers in the processed fascia.

Figure 11:
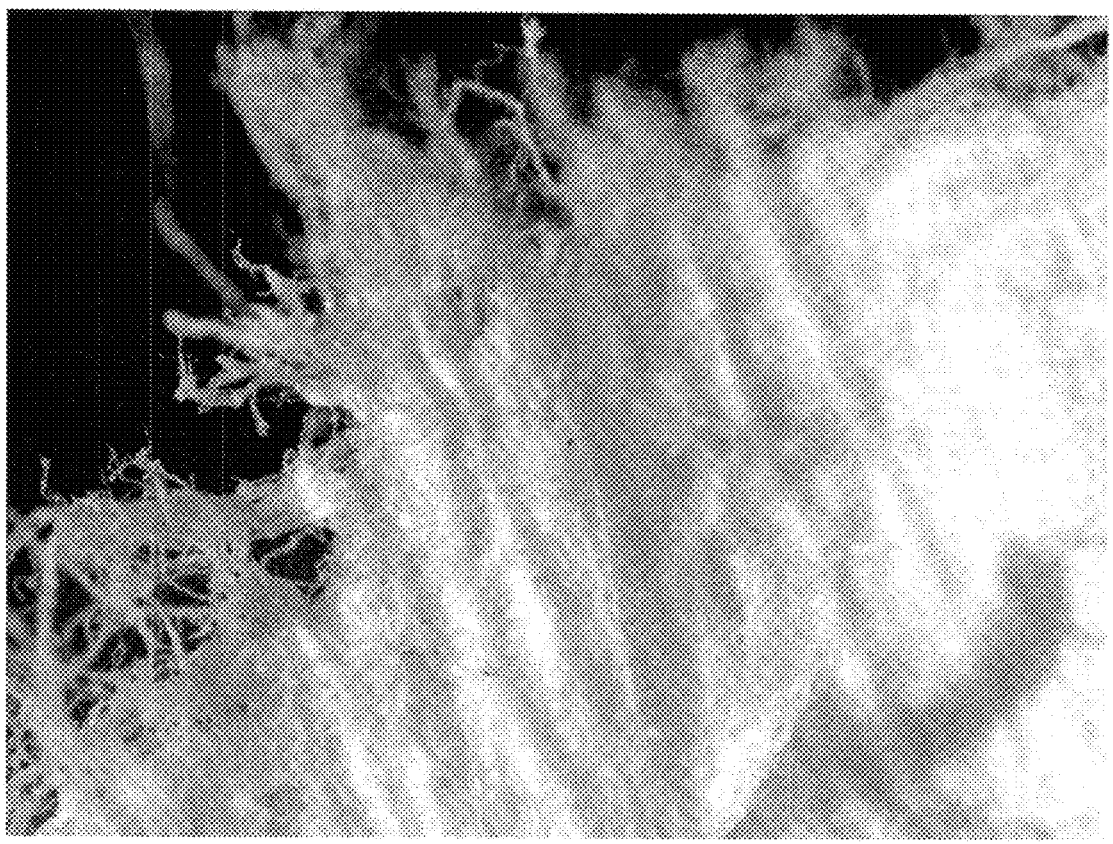
FIG. 11 provides a 0.5× magnification view of an edge of the processed fascia tissue.

FIG. 11 provides a 0.5× magnification view of an edge of the processed fascia tissue, which depicts the fibrous nature of the fascia and the spider web-like sheet.

Figure 12:
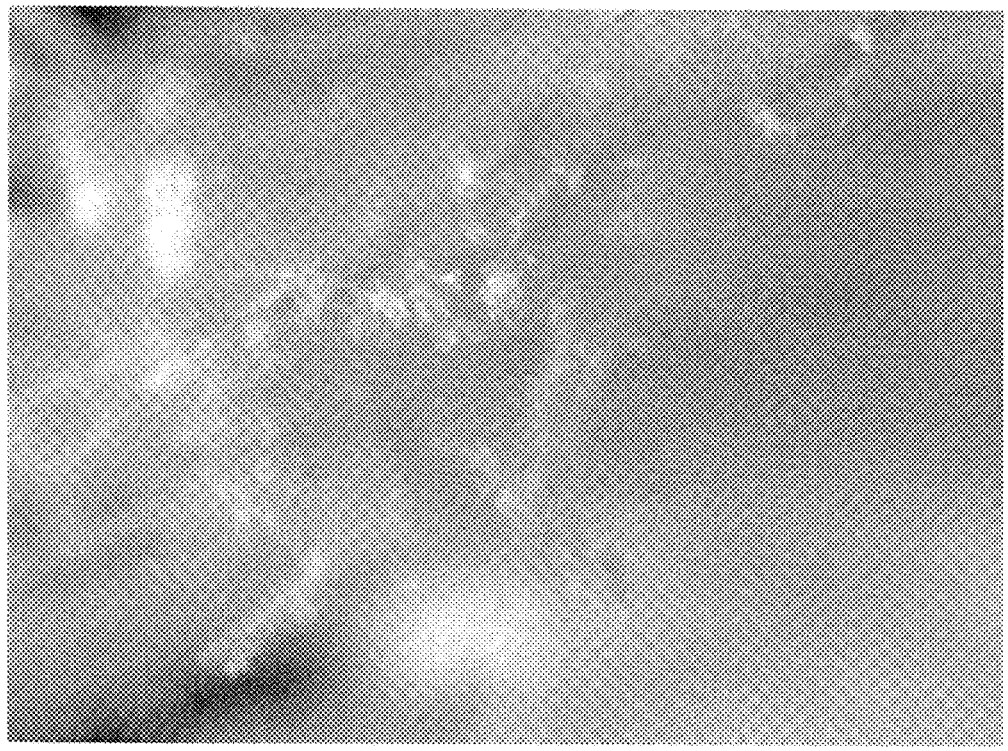
FIG. 12 shows a 0.5× magnification view of processed fascia tissue.
Figure 13:
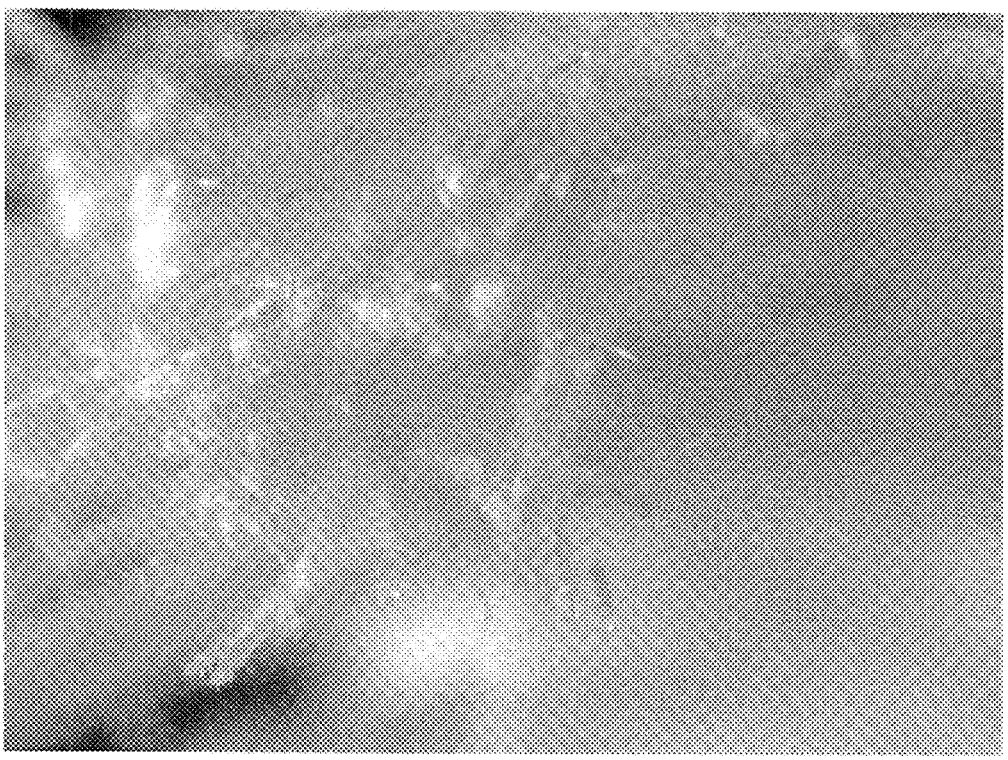
FIG. 13 shows a 0.5× magnification view of processed fascia tissue.
Figure 14:
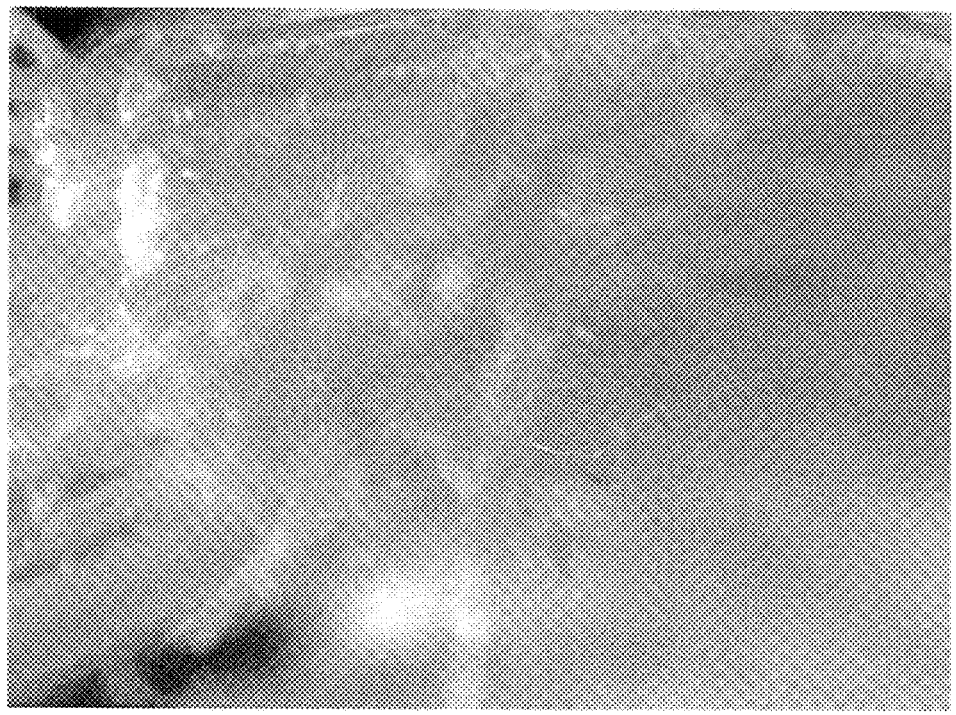
FIG. 14 shows a 0.5× magnification view of processed fascia tissue.

FIGS. 12, 13, and 14 each show a 0.5× magnification view of processed fascia tissue, depicting fiber ends of major fibers.

Figure 15:
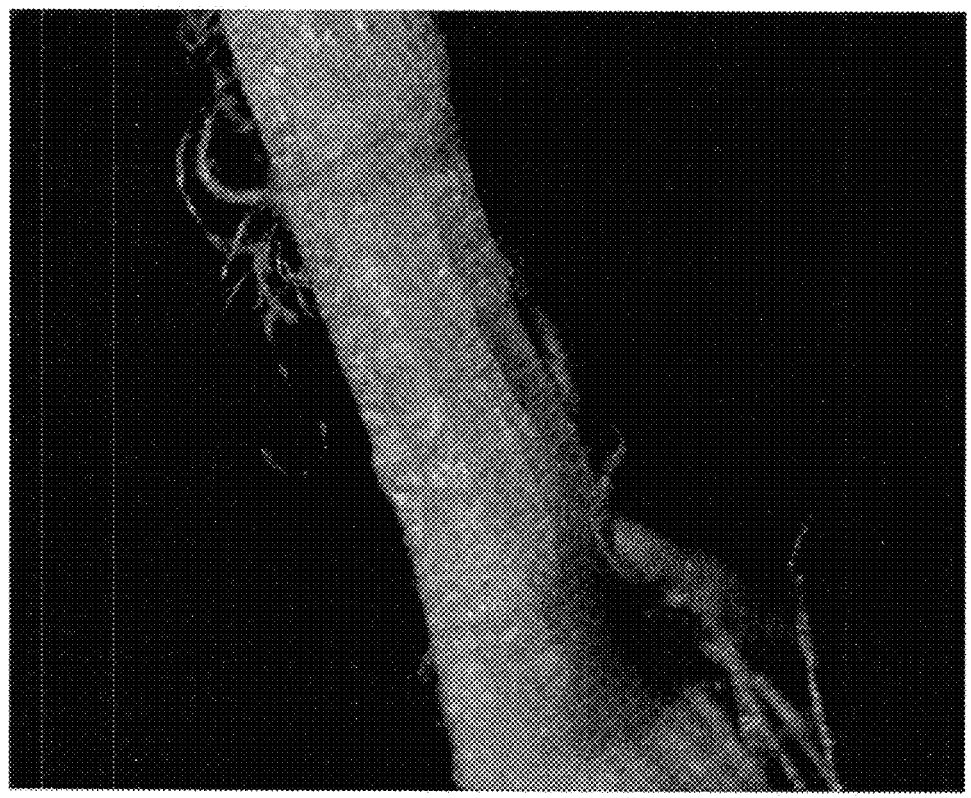
FIG. 15 shows a 10× magnification view of processed fascia tissue.
Figure 16:
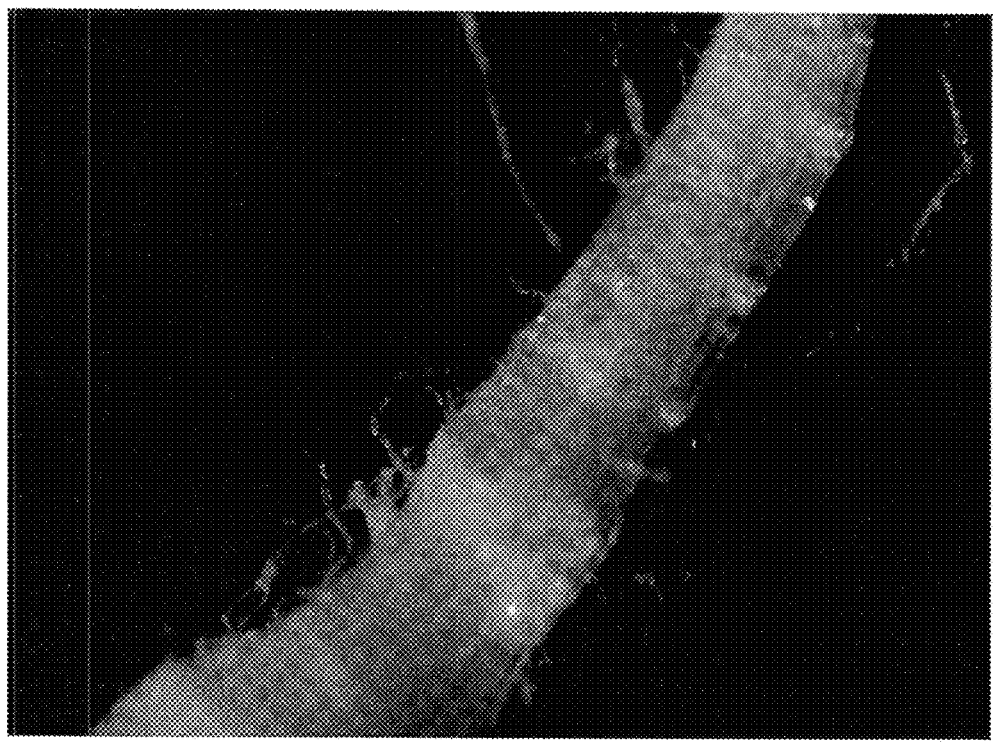
FIG. 16 shows a 100× magnification view of processed fascia tissue.
Figure 17:
FIG. 17 shows a 10× magnification view of processed fascia tissue.

FIGS. 15, 16, and 17 each show a 10× magnification view of processed fascia tissue, depicting major fiber stalks.

Figure 18:
FIG. 18 provides a 10× magnification view of a tweezer pulled fascia fibers.
Figure 19:
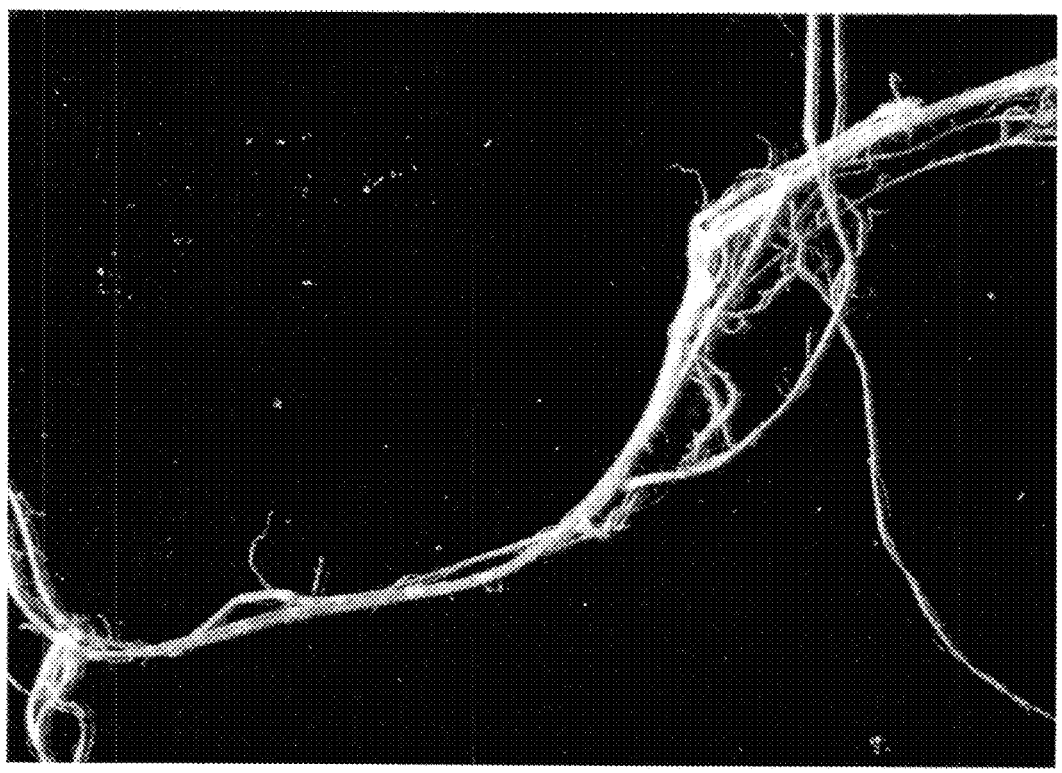
FIG. 19 provides a 0.5× magnification view of a pulled major fiber.

FIG. 18 provides a 10× magnification view of a tweezer pulled fascia fibers, having a diameter of about 12 microns. FIG. 19 provides a 0.5× magnification view of a pulled major fiber, having a diameter of about 100 microns. As discussed elsewhere herein, such fibers can be extracted from the natural fascia anatomy. Once extracted, the fibers can be further processed like a textile fiber. The fibers can then be manufactured into sheets, bundles e.g. (yarn), or 3 dimensional structures.

Figure 20:
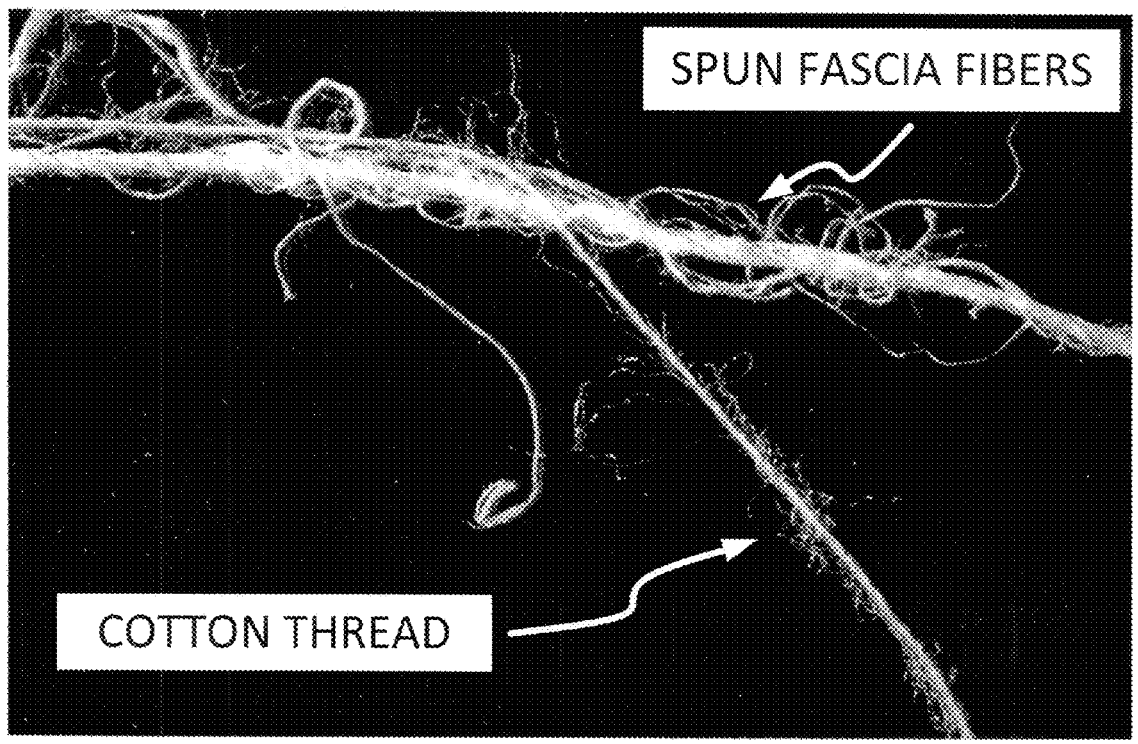
FIG. 20 shows a 0.5× magnification of spun fascia fibers, compared to a standard cotton thread.

FIG. 20 shows a 0.5× magnification of spun fascia fibers, compared to a standard cotton thread.

Figure 21:
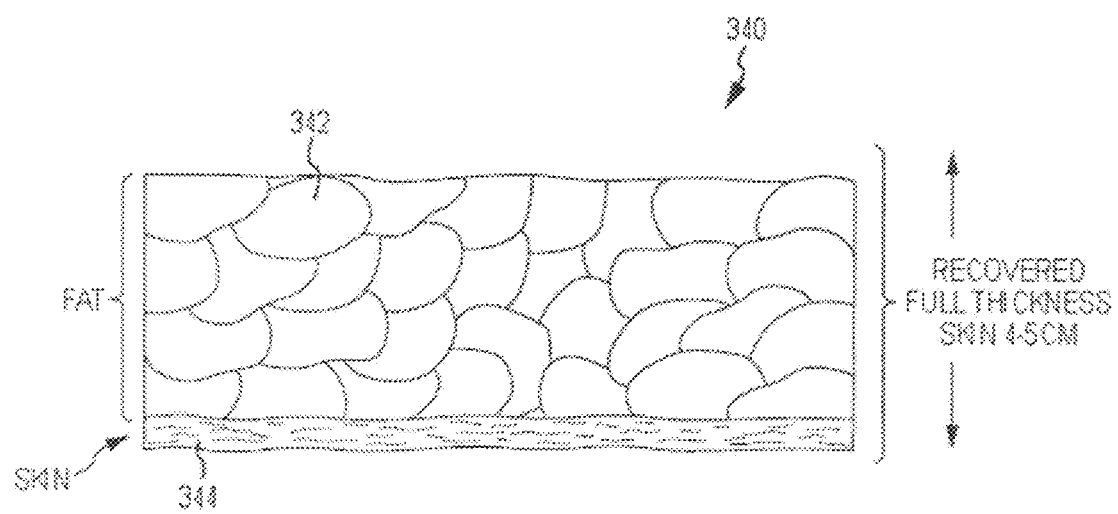
FIG. 21 shows an illustration of skin and fat tissue according to embodiments of the present invention.

Embodiments of the invention may encompass fibers from the body other than fascia fibers. For example, fat fibers or dermis fibers could be used. These fibers may be collagen fibers. FIG. 21 provides an illustrative example of skin and fat tissue. As depicted here, a portion of full thickness skin 340 can be recovered from a donor. The portion of full thickness skin 340 can have a thickness of about 4 to 5 cm, for example, and can include both fat component 342 and skin component 344. Processing of the portion of the full thickness skin 340 can result in a removed portion of dermis and a remaining portion or slab of fat (for example having a thickness within a range from about 1 cm to about 5 cm).

Figure 22:
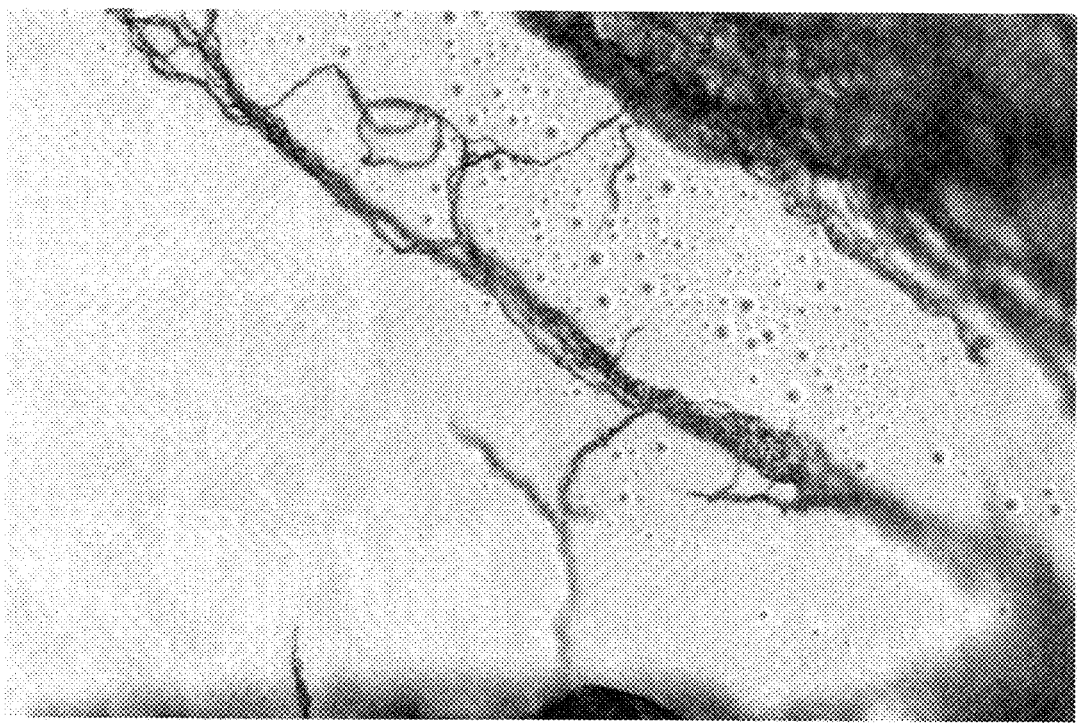
FIG. 22 shows a 100× magnification of a bundle of fat fibers on a slide after multiple washings with acetone.

Fat fibers could come from the back of a cadaver. Such fat may include dermal or subdermal fat. FIG. 22 shows a 10× magnification of a bundle of fat fibers on a slide after multiple washings of fibers in an adipose fat matrix with acetone. In this case, it was discovered that two washings of 15 minutes each in a beaker of acetone with agitation failed to remove all the oils. As shown in the figure, when the bundle of fibers was placed on a slide, oil droplets were also observed on the glass surface. Leaving residual oil in the fibers may have negative effects on machinery used to process or handle the fibers. Residual oil may be transferred to such machinery and require additional cleanings of the machinery, unnecessary downtime, and/or reduced throughput.

Figure 23:
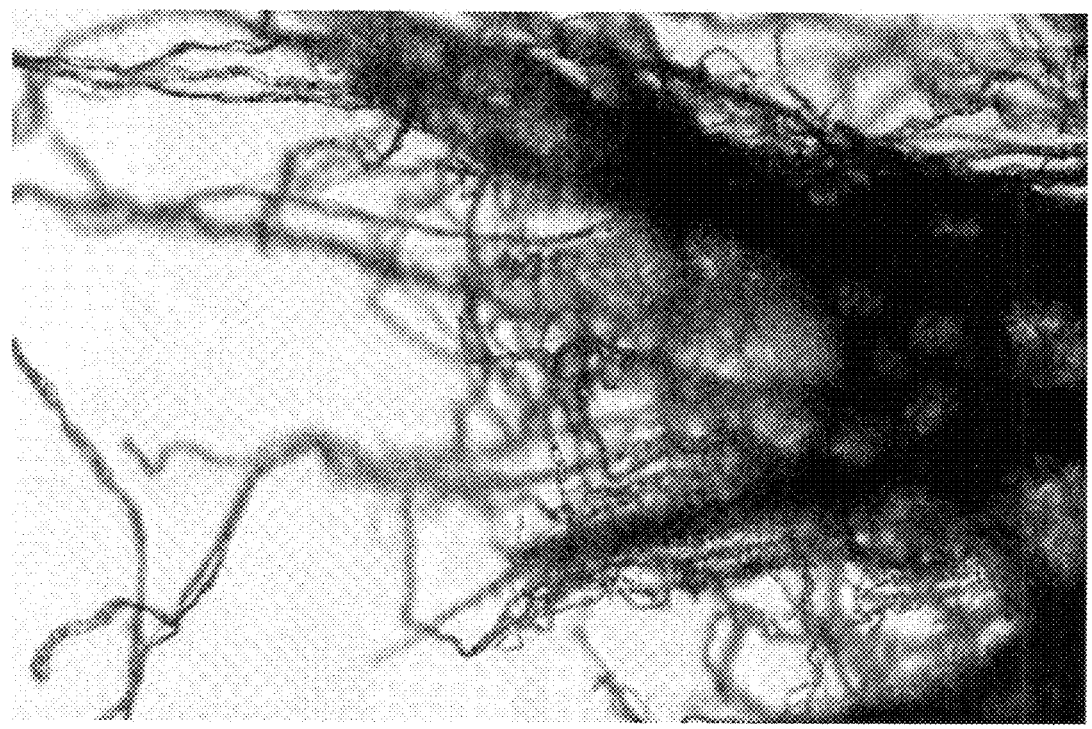
FIG. 23 shows a 10× magnification of a bundle of fat fibers after multiple washings with acetone and then an additional washing with hexane.

FIG. 23 shows a 10× magnification of the bundle of fat fibers in FIG. 22 after an additional washing with hexane. Oil droplets were not observed after this washing. Hexane may have removed all oils from the fascia fibers. Fat fibers in this case may be discernible and separable.

Figure 24:
FIG. 24 shows a sample of fascia treated with acetone and a sample of fascia treated with hexane.

FIG. 24 shows a sample of fascia treated with acetone (top) and a sample of fascia treated with hexane (bottom). Both samples were washed for 15 minutes. With the sample treated with hexane, no discernible fibers could be observed even under magnification. The fascia treated with hexane had a plastic-like appearance, without any discernible fibers. This may make separating fibers difficult or impossible. In the bottom sample, the acetone may remove the oils but leave behind a dry matrix, which may have fibers that may be easily separable.

Figure 25:
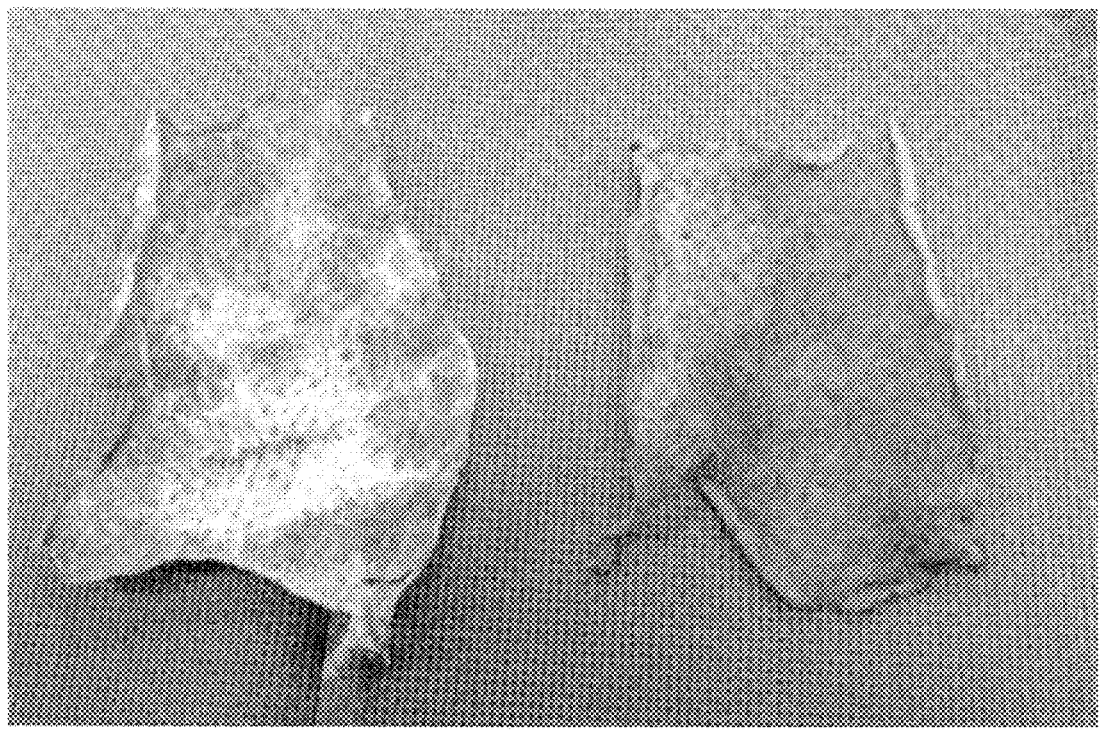
FIG. 25 shows a sample of human dermis treated with acetone and a sample of human dermis treated with hexane.

Embodiments of the invention may encompass dermis tissue. FIG. 25 shows a sample of human dermis treated with acetone (left) and a sample of human dermis treated with hexane (right). The effect of hexane on human dermis may appear less severe than on fascia. However, as with the sample of fascia treated with hexane in FIG. 24, in this sample of human dermis treated with hexane, the fibers are not easily separable. The sample of human dermis treated with hexane had a leather-like appearance, without any discernible fibers. Fibers in human dermis may be shorter than fibers from fascia or fat.

Tissues were washed with different solvents to determine the solvents' effects. Fascia was washed with isopropyl alcohol, and isopropyl alcohol was observed to minimally extract oils from the fascia. Another solvent, acetonitrile, was used to wash fascia and dermis tissue and was able to remove substantially all of the residual oil. However, when used to wash fat fibers, acetonitrile was observed to not remove all of the residual oil. Without intending to be bound by theory, it is hypothesized that oil may be harder to remove from fat tissue because such fibers may be bonded or attracted to oil at a molecular level, while fibers in fascia tissue and dermis tissue are not bonded or attracted to oil in the same way.

Figure 26:
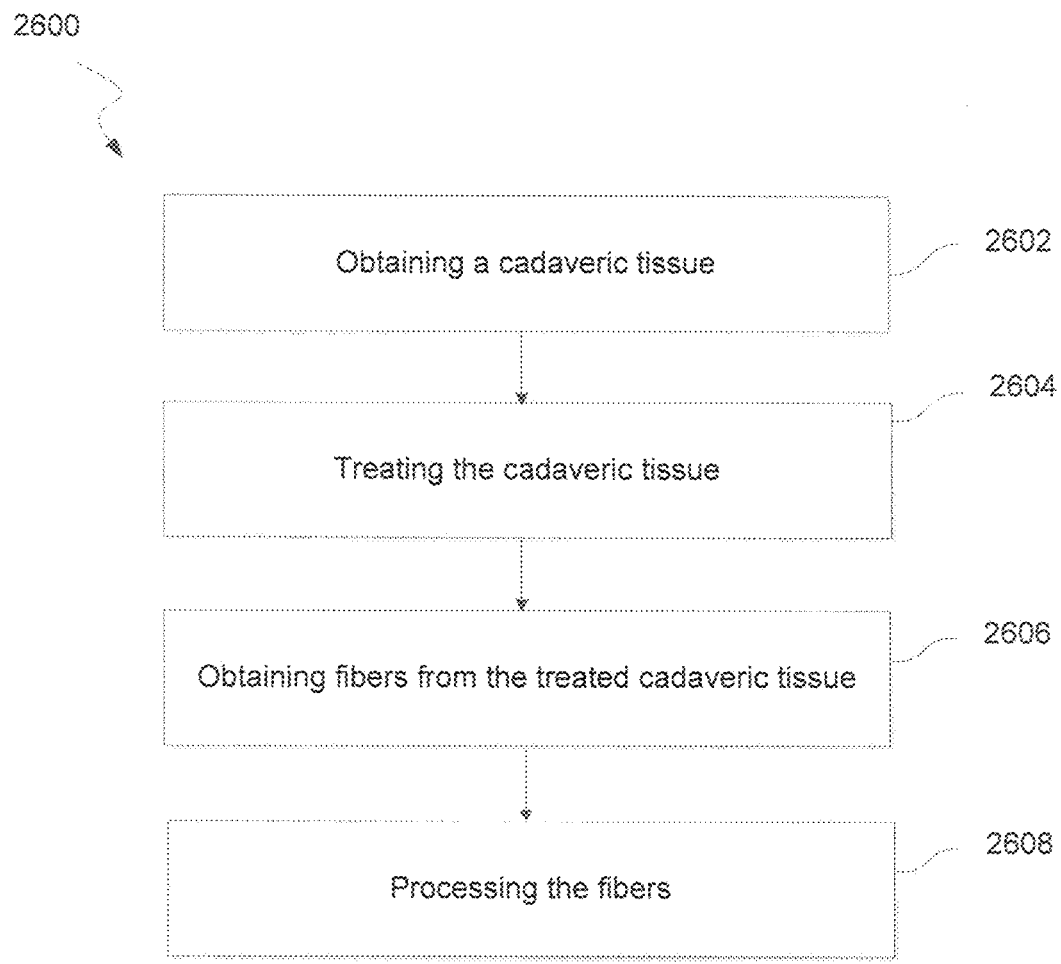
FIG. 26 shows steps in a method of producing a fibrous biotextile composition according to embodiments of the present invention.

FIG. 26 shows steps in a method 2600 of producing a fibrous fascia biotextile composition according to embodiments of the present invention. The method 2600 may include obtaining a cadaveric tissue 2602. In these or other embodiments, the method 2600 may include treating the cadaveric tissue 2604. In some cases, the method 2600 may include obtaining fibers from the treated cadaveric tissue 2606. The method 2600 may include processing the fibers 2608.

Figure 27:
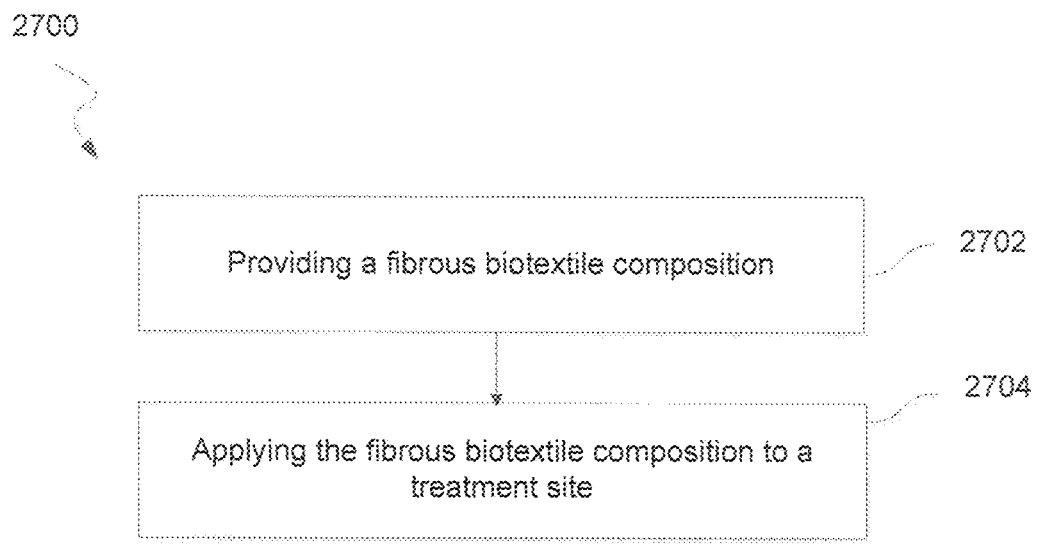
FIG. 27 shows steps in a method of treating a patient according to embodiments of the present invention.

FIG. 27 shows steps in a method 2700 of treating a patient according to embodiments of the present invention. The method 2700 may include providing a fibrous biotextile composition 2702. In these or other embodiments, the method 2700 may include applying the fibrous biotextile composition to a treatment site 2704.

Any of a variety of textile and threadmaking processes can be used to process the fibrous fascia tissue structures disclosed herein. For example, fibers or filaments obtained from processed fascia tissue can be used to manufacture sheets, bundles, and other three dimensional fibrous structures of collagen origin. According to some embodiments, such manufactured compositions may be referred to as biotextiles.

According to some embodiments, human cadaveric fascia fibers and filaments, for example having a high tensile strength, can be manufactured into bundles or bundle-like configurations, such as threads, yarns, twines, ropes, sutures, and the like. According to some embodiments, human cadaveric fascia fibers and filaments can be manufactured into woven sheet or other woven or nonwoven (e.g. needle-punched or entangled) configurations, such as meshes, and woven textiles such as blankets or felts. According to some embodiments, human cadaveric fascia fibers and filaments can be manufactured into three dimensional layered configurations or matrices, so as to provide flexible and/or movable fiber configurations. Hence, embodiments of the present invention encompass any of a variety of techniques for processsing a biological derived fiber source of human fascia origin that is a precursor to multiple textile configurations.

According to some embodiments, fibrous collagen structures can be used as a source of collagen for repairing damaged collagen containing tissue such as tendons, muscle, ligaments, and some forms of cartilage. In some cases, fascia fibrous materials can be used in wound repair applications. In some cases, fascia fibrous materials can be used as a natural suture, mesh, fabric, or other biological implant or device. In some cases, fascia fibrous materials can be used in patient treatment sites that may be susceptible to scarring. In some cases, fascia fibrous materials can be used at a patient treatment site to serve as a temporary scaffold while the natural body regenerates.

Embodiments of the present invention encompass the use of standard textile processing methods for developing biotextiles and other materials containing natural human collagen fibers obtained from fascia. Relatedly, fascia tissue fibers can be extracted, treated, and/or reassembled according to any of a variety of techniques to produce biotextile compositions.

Because of the unique strength and availability of a fascia fiber that when processed becomes a textile-like starting material, such fibers can be used for any of a variety of applications. In this way, the biotextile technology described herein encompasses the use of donated tissue for the production of fiber (e.g. larger primary fibers and/or smaller spider web-like fibers) which can be formed into a textile based material.

According to some embodiments, fascia biotextile configurations as discussed herein can be augmented by adding, incorporating, or otherwise combining any of a variety of biological components such as stem cell compositions, polymer based supports or skeletons, bone constructs (e.g. nondemineralized, partially demineralized, or fully demineralized) containing cortical and/or cancellous bone material, such as compositions described in U.S. patent application Ser. No. 12/612,583 filed Nov. 4, 2009, Ser. No. 13/680,222 filed Nov. 19, 2012, and 61/774,036 filed March 7, the contents of each of which are incorporated herein by reference, with the fascia fibrous structures. In some cases, fibrous fascia structures can be provides as nonwoven, woven, or threaded materials for use in surgery, such as sutures, mats, felts, pads, and the like. According to some embodiments, biotextile threads, meshes, and the like may be provided with a desirable tensile strength and/or elasticity, which may originate from the tensile strength and/or elasticity of collagen fibers which are present in the biotextile.

As discussed elsewhere herein, fascia fibrous structures may be provided in various sizes and dimensions. For example, fascia fibers have been isolated and observed to be present in lengths in excess of 20 cm long with diameters as low as approximately 5 microns.

Fascia fibers as discussed herein can be prepared or processed according to any of a variety of extraction and production techniques. For example, fibers may be carded, spun, woven, and the like. Exemplary biotextile configurations include gauzes, meshes (e.g. for hernia treatment), implants for use in facial ligament and/or tendon re-construction, ligament/tendon bundles, fabric wraps, fabric clamps (e.g. resembling a hose clamp), sutures, and the like. Hence, fascia fiber biotextiles can be used for hernia mesh procedures, tendon replacement, and for the repair of torn tendons (e.g. as fascia sutures). In some cases, fascia fiber biotextiles can be applied to a bleeding site to inhibit bleeding or absorb blood.

All patents, patent publications, patent applications, journal articles, books, technical references, and the like discussed in the instant disclosure are incorporated herein by reference in their entirety for all purposes.

It is to be understood that the figures and descriptions of the invention have been simplified to illustrate elements that are relevant for a clear understanding of the invention. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A method of producing a fibrous fascia biotextile composition, the method comprising:
obtaining a deceased donor fascia tissue;
treating the deceased donor fascia tissue with acetone;

obtaining intact fascia fibers from the treated deceased donor fascia tissue, wherein the intact fascia fibers have a diameter from 5 to 200 microns and a length greater than 20 cm; and processing the intact fascia fibers to produce the fibrous fascia biotextile using a textile or threadmaking process.

2. The method of claim 1, wherein the method further comprises washing and clearing the deceased donor fascia tissue of biological fluids.

3. The method of claim 1, wherein the method further comprises exposing the deceased donor fascia tissue to a basic solution and an organic dehydrating solution before treating the deceased donor fascia tissue with acetone.

4. The method of claim 1, wherein the deceased donor fascia tissue comprises adipose oil and the method further comprises removing substantially all of the adipose oil.

5. The method of claim 1, wherein processing the intact fascia fibers comprises weaving, bundling, spinning, or carding.

6. The method of claim 1, wherein the fibrous fascia biotextile comprises sheets, bundles, or other three dimensional fibrous structures.

7. The method of claim 1, wherein the fibrous fascia biotextile comprises movable fiber configurations.

8. The method of claim 1, wherein the method further comprises adding a biological component selected from the group consisting of a stem cell composition, a polymer based support, a polymer based skeleton, and a bone construct to the fibrous fascia biotextile.

9. The method of claim 1, wherein the fibrous fascia biotextile comprises sutures, mats, felts, or pads for use in surgery.

10. The method of claim 1, wherein the fibrous fascia biotextile comprises gauzes, meshes, implants for use in facial ligament or tendon reconstruction, ligament/tendon bundles, fabric wraps, or fabric clamps.

11. The method of claim 1, further comprising washing the deceased donor fascia tissue with hexane after treating the deceased donor fascia tissue with acetone.

12. The method of claim 1, wherein treating the deceased donor fascia tissue with acetone comprises a plurality of washings with acetone.

13. The method of claim 1, wherein treating the deceased donor fascia tissue with acetone comprises treating the deceased donor tissue with a single organic solvent consisting of acetone.

14. The method of claim 13, further comprising washing the deceased donor fascia tissue with hexane after treating the deceased donor fascia tissue with acetone.

15. The method of claim 1, wherein the intact fascia fibers are non-denatured.

16. The method of claim 1, wherein processing the intact fascia fibers to produce the fibrous fascia biotextile comprises using the textile process.

17. The method of claim 1, wherein processing the intact fascia fibers to produce the fibrous fascia biotextile comprises using the threadmaking process.

18. The method of claim 1, wherein processing the intact fascia fibers comprises weaving.

19. The method of claim 1, wherein processing the intact fascia fibers comprises bundling.

20. The method of claim 1, wherein processing the intact fascia fibers comprises spinning.

21. The method of claim 1, wherein processing the intact fascia fibers comprises carding.

22. The method of claim 1, wherein the fibrous fascia biotextile comprises sheets.

23. The method of claim 1, wherein the fibrous fascia biotextile comprises bundles.

24. The method of claim 1, wherein the fibrous fascia biotextile comprises three dimensional fibrous structures.

25. The method of claim 1, wherein the method further comprises adding a stem cell composition to the fibrous fascia biotextile.

26. The method of claim 1, wherein the method further comprises adding a polymer based support to the fibrous fascia biotextile.

27. The method of claim 1, wherein the method further comprises adding a polymer based skeleton to the fibrous fascia biotextile.

28. The method of claim 1, wherein the method further comprises adding a bone construct to the fibrous fascia biotextile.

29. The method of claim 1, wherein the fibrous fascia biotextile comprises gauzes.

30. The method of claim 1, wherein the fibrous fascia biotextile comprises meshes.

31. The method of claim 1, wherein the fibrous fascia biotextile comprises implants for use in facial ligament or tendon reconstruction.

32. The method of claim 1, wherein the fibrous fascia biotextile comprises ligament bundles.

33. The method of claim 1, wherein the fibrous fascia biotextile comprises tendon bundles.

34. The method of claim 1, wherein the fibrous fascia biotextile comprises fabric wraps.

35. The method of claim 1, wherein the fibrous fascia biotextile comprises fabric clamps.

* * * * *